United States Patent
Wang et al.

(10) Patent No.: US 11,318,097 B1
(45) Date of Patent: May 3, 2022

(54) ROS-RESPONSIVE MULTILAMELLAR LIPOSOMAL VESICLES FOR TARGETING INFLAMMATORY MACROPHAGES

(71) Applicant: Verily Life Sciences LLC, South San Francisco, CA (US)

(72) Inventors: Zhan Wang, San Jose, CA (US); Stephen Morton, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 16/750,910

(22) Filed: Jan. 23, 2020

Related U.S. Application Data

(62) Division of application No. 15/672,589, filed on Aug. 9, 2017, now Pat. No. 10,583,083.

(60) Provisional application No. 62/372,986, filed on Aug. 10, 2016.

(51) Int. Cl.
  *A61K 9/127* (2006.01)
(52) U.S. Cl.
  CPC ............ *A61K 9/127* (2013.01); *A61K 9/1277* (2013.01); *Y10S 977/906* (2013.01); *Y10S 977/907* (2013.01)
(58) Field of Classification Search
  None
  See application file for complete search history.

(56) References Cited

U.S. PATENT DOCUMENTS

| | | | |
|---|---|---|---|
| 3,130,009 A | 4/1964 | Brotherton | |
| 5,891,468 A | 4/1999 | Martin et al. | |
| 10,106,650 B2 * | 10/2018 | Lam | A61P 37/08 |
| 10,517,823 B1 | 12/2019 | Kam et al. | |
| 10,583,083 B1 * | 3/2020 | Wang | A61K 47/50 |
| 2006/0153907 A1 * | 7/2006 | Zalipsky | A61K 9/1271 424/450 |

(Continued)

FOREIGN PATENT DOCUMENTS

CN 103755839 4/2014

OTHER PUBLICATIONS

JJ Moon et al. "Interbilayer-crosslinked multilamellar vesicles as synthetic vaccines for potent humoral and cellular immune responses." Nature Materials, vol. 10, Mar. 2011, pp. 243-251. (Year: 2011).*

(Continued)

*Primary Examiner* — Isaac Shomer
(74) *Attorney, Agent, or Firm* — Kilpatrick Townsend & Stockton LLP

(57) ABSTRACT

Provided herein are liposomal vesicles comprising at least a first lipid bilayer and a second lipid bilayer, and a plurality of crosslinkages between the first lipid bilayer and the second lipid bilayer, wherein the plurality of crosslinkages comprise boronic ester or thioketal bonds. Also provided are pharmaceutical compositions comprising the liposomal vesicles described herein and a pharmaceutically acceptable excipient. Also provided are methods of making and using the liposomal vesicles. Thus, a method of treating a subject with a disease comprising administering to the subject a pharmaceutical composition comprising the liposomal vesicles is described herein. Methods of making multilamellar liposomal vesicles responsive to reactive oxygen species are also provided.

20 Claims, 1 Drawing Sheet

(56) References Cited

U.S. PATENT DOCUMENTS

| | | | |
|---|---|---|---|
| 2007/0116753 | A1 | 5/2007 | Hong et al. |
| 2009/0175873 | A1 | 7/2009 | Liu |
| 2012/0058177 | A1 | 3/2012 | Reisfeld et al. |
| 2014/0308212 | A1 | 10/2014 | Zhang et al. |
| 2015/0342883 | A1 | 12/2015 | Cheng et al. |

OTHER PUBLICATIONS

MS Shim, Y Xia. "A Reactive Oxygen Species (ROS)-Responsive Polymer for Safe, Efficient, and Targeted Gene Delivery in Cancer Cells." Angewandte Communications International Edition, vol. 52, 2013, pp. 6926-6929. (Year: 2013).*

Yarong Liu, Jinxu Fang, Yu-Jeong Kim, Michael K. Wong, and Pin Wang. "Codelivery of Doxorubicin and Paclitaxel by Cross-Linked Multilamellar Liposome Enables Synergistic Antitumor Activity." Molecular Pharmaceutics, vol. 11, 2014, pp. 1651-1661. (Year: 2014).*

James J. Moon et al. "Interbilayer-crosslinked multilamellar vesicles as synthetic vaccines for potent humoral and cellular immune responses." Nature Materials, vol. 10, Mar. 2011, pp. 243-251. (Year: 2011).*

Jonathan D. Ashley, Jared F. Stefanick, Valerie A. Schroeder, Mark A. Suckow, Tanyel Kiziltepe, and Basar Bilgicer. "Liposomal Bortezomib Nanoparticles via Boronic Ester Prodrug Formulation for Improved Therapeutic Efficacy in Vivo." Journal of Medicinal Chemistry, vol. 57, 2014, pp. 5282-5292. (Year: 2014).*

J. N. Israelachvili, S. Marcelja, and R. G. Horn. "Physical principles of membrane organization." Quarterly Reviews of Biophysics 13, 2 (1980), pp. 121-200. (Year: 1980).*

Jacopo Sforzi, Lorenzo Palagi and Silvio Aime. "Liposome-Based Bioassays." Biology, vol. 9(202), 2020, pp. 1-25. (Year: 2020).*

Diego Voccia, Francesca Bettazzi, Emiliano Fratini, Debora Berti, and Ilaria Palchetti. "Improving impedimetric nucleic acid detection by using enzyme-decorated liposomes and nanostructured screen-printed electrodes." Analytical and Bioanalytical Chemistry, vol. 408, 2016, pp. 7271-7281. (Year: 2016).*

Li, L., et al. "Boronate-dextran: An acid-responsive biodegradable polymer for drug delivery", Biomaterials, vol. 34, Issue 33, https://doi.org/10.1016/j.biomaterials.2013.07.053, Aug. 7, 2013, pp. 8504-8510.

Notice of Allowance dated Nov. 25, 2019 in U.S. Appl. No. 15/672,589, all pages.

"Polypropylene Glycol", Available Online at: https://www.sigmaaldrich.com/catalog/product/aldrich/81380?lang=en&region=IN, Accessed from Internet on Aug. 5, 2019, 3 pages.

U.S. Appl. No. 15/672,589, "Final Office Action", dated May 14, 2019, 20 pages.

U.S. Appl. No. 15/672,589, "Non-Final Office Action", dated Jan. 17, 2019, 14 pages.

U.S. Appl. No. 15/672,589, "Non-Final Office Action", dated Aug. 13, 2019, 17 pages.

U.S. Appl. No. 15/672,589, "Notice of Allowance", dated Nov. 25, 2019, 13 pages.

U.S. Appl. No. 15/672,589, "Restriction Requirement", dated Oct. 9, 2018, 12 pages.

U.S. Appl. No. 15/672,591, "Final Office Action", dated May 6, 2019, 13 pages.

U.S. Appl. No. 15/672,591, "Non-Final Office Action", dated Jan. 23, 2019, 15 pages.

U.S. Appl. No. 15/672,591, "Notice of Allowance", dated Sep. 3, 2019, 16 pages.

U.S. Appl. No. 15/672,591, "Restriction Requirement", dated Oct. 19, 2018, 11 pages.

Akbarzadeh et al., "Liposome: classification, preparation, and applications", Nanoscale research letters, vol. 8.1, 2013, 102 pages.

Allen et al., "Anti-CD19-Targeted Liposomal Doxorubicin Improves the Therapeutic Efficacy in Murine B-Cell Lymphoma and Ameliorates the Toxicity of Liposomes with Varying Drug Release Rates", Clin Cancer Res., Cancer Therapy: Preclinical, vol. 11, No. 9, May 1, 2005, pp. 3567-3573.

Alli et al., "Synthesis, Characterization and Surface Properties of Amphiphilic Polystyrene-B-Polypropylene Glycol Block Copolymers", European Polymer Journal, vol. 42, Issue 4, Apr. 2006, pp. 740-750.

Amoozgar et al., "Targeting myeloid cells using nanoparticles to improve cancer immunotherapy", Advanced drug delivery reviews 91 (2015): 38-51 (abstract only).

Ashley et al., "Liposomal Bortezomib Nanoparticles via Boronic Ester Prodrug Formulation for Improved Therapeutic Efficacy in Vivo", Journal of medicinal chemistry, vol. 57, Issue 12, 2014, pp. 5282-5292.

Boomer et al., "Cytoplasmic delivery of liposomal contents mediated by an acid-labile cholesterol-vinyl ether-PEG conjugate", Bioconjugate chemistry 20.1 (2008): 47-59.

Bozzuto et al., "Liposomes as Nanomedical Devices", International Journal of Nanomedicine, vol. 10, 2015, 975 pages.

Bull et al., "Exploiting the Reversible Covalent Bonding of Boronic Acids: Recognition, Sensing, and Assembly", Accounts of Chemical Research, vol. 46, No. 2, 2013, pp. 312-326.

Charrois et al., "Drug Release Rate Influences the Pharmacokinetics, Biodistribution, Therapeutic Activity, and Toxicity of Pegylated Liposomal Doxorubicin Formulations in Murine Breast Cancer", Biochimica et Biophysica Acta, vol. 1663, No. 1-2, www.sciencedirect.com, May 27, 2004, pp. 167-177.

Chawla et al., "Macrophage-mediated inflammation in metabolic disease", Nature reviews. Immunology 11.11 (2011): 738-749.

Cummings et al., "Tetrahydroxydiboron-Mediated Palladium-Catalyzed Transfer Hydrogenation and Deuteriation of Alkenes and Alkynes Using Water as the Stoichiometric H or D Atom Donor", Journal of the American Chemical Society, vol. 138, No. 9, May 2016, pp. 6107-6110.

Daniel et al., "Dual-responsive nanoparticles release cargo upon exposure to matrix metalloproteinase and reactive oxygen species", Chemical Communications, vol. 52, Issue 10, 2016, pp. 2126-2128.

Dasgupta et al., "Non inflammatory boronate based glucose-responsive insulin delivery systems", PloS One, vol. 7.1: e29585, 2012.

Davis et al., "Nanoparticle therapeutics: an emerging treatment modality for cancer", Nature reviews. Drug discovery 7.9 (2008): 771 (abstract only).

Etzerodt et al., "CD163 and Inflammation: Biological, Diagnostic, and Therapeutic Aspects", Antioxidants & Redox Signaling, vol. 18, Issue 17, 2013, pp. 2352-2363.

Fang et al., "Cleavable PEGylation: a Strategy for Overcoming the "PEG Dilemma" in Efficient Drug Delivery", Drug Delivery, vol. 24, No. 2, Dec. 2017, pp. 22-32.

Germano et al., "Role of macrophage targeting in the antitumor activity of trabectedin", Cancer cell 23.2 (2013): 249-262.

Graversen et al., "Drug Trafficking Into Macrophages via the Endocytotic Receptor CD163", Membranes, vol. 5, No. 2, Jun. 23, 2015, pp. 228-252.

Grosse et al., "Tumor-specific gene transfer with receptor-mediated nanocomplexes modified by polyethylene glycol shielding and endosomally cleavable lipid and peptide linkers", The FASEB Journal 24.7 (2010): 2301-2313.

Irvine et al., "Synthetic nanoparticles for vaccines and immunotherapy", Chemical reviews 115.19 (2015): 11109-11146.

Jeong et al., "Reactive oxygen species responsive drug releasing nanoparticle based on chondroitin sulfate-anthocyanin nanocomplex for efficient tumor therapy", Journal of Controlled Release 222 (2016): 78-85 (abstract only).

Joo et al., "Crosslinked Multilamellar Liposomes for Controlled Delivery of Anticancer Drugs", Biomaterials, vol. 34, No. 12, Apr. 2013, pp. 3098-3109.

Larkin et al., "Structure of the Boronic Acid Dimer and the Relative Stabilities of Its Conformers", Journal of Physical Chemistry A, vol. 110, No. 36, 2006, pp. 10633-10642.

(56) References Cited

OTHER PUBLICATIONS

Li et al., "Boronateedextran: An Acid-Responsive Biodegradable Polymer for Drug Delivery", Biomaterials, vol. 34, No. 33, 2013, pp. 8504-8510.

Liang et al., "ROS-Responsive Drug Delivery Systems", Bioengineering & Translational Medicine, vol. 1, No. 3, Sep. 2016, pp. 239-251.

Liu et al., "Legumain protease-activated TAT-liposome cargo fortargeting tumours and their microenvironment", Nature communications, vol. 5, 2014, 4280 pages.

Love et al., "Efficient clodronate entrapment within multilamellar and unilamellar liposomes", Journal of pharmacological and toxicological methods 27.3 (1992): 185-189 (abstract only).

Lux et al., "Biocompatible Polymeric Nanoparticles Degrade and Release Cargo in Response to Biologically Relevant Levels of Hydrogen Peroxide", Journal of the American Chemical Society, vol. 134, No. 38, Sep. 4, 2012, pp. 15758-15764.

Minikel, "Organic Chemistry 08: Carbonyl Conjugation, Conformational Analysis, Cyclic Compounds", www.cureffi.org/2015/02/13/organic-chemistry-08/, Feb. 13, 2015, 9 pages.

Mo et al., "Tumor microenvironment and intracellular signal-activated nanomaterials for anticancer drug delivery", Materials Today 19.5 (2016): 274-283.

Moon et al., "Interbilayer-crosslinked multilamellar vesicles as synthetic vaccines for potent humoral and cellular immune responses", Nature materials 10.3 (2011): 243-251.

Murray et al., "Protective and pathogenic functions of macrophage subsets", Nature reviews immunology 11.11 (2011): 723-737.

Olympus, "Improving Drug Delivery with Macrophage Targeting", May 16, 2013.

Rowan et al., "Dynamic Covalent Chemistry", Angewandte Chemie International Edition, vol. 41, 2002, pp. 899-952.

Ruffell et al., "Macrophages and therapeutic resistance in cancer", Cancer cell 27.4 (2015): 462-472.

Saravolac et al., "Effect of liposome-encapsulation on immunomodulating and antiviral activities of interferon-$\gamma$", Antiviral research, vol. 29, 1996, pp. 199-207.

Shim et al., "A Reactive Oxygen Species (ROS)-Responsive Polymer for Safe, Efficient, and Targeted Gene Delivery in Cancer Cells", Angewandte Chemie International Edition 52.27 (2013): 6926-6929.

Sun, Xiaolong, et al. "The mechanisms of boronate ester formation and fluorescent turn-on in ortho-aminomethylphenylboronic acids." *Nature chemistry* 11.9 (2019): 768-778.

Suzuki, "Recent Advances in the Cross-Coupling Reactions of Organoboron Derivatives with Organic Electrophiles, 1995-1998", Journal of Organometallic Chemistry, vol. 576, Nos. 1-2, Mar. 15, 1999, pp. 147-168.

Takeshima et al., "Ratiometric Sensing of Hydrogen Peroxide Utilizing Conformational Change in Fluorescent Boronic Acid Polymers", Journal of Analytical Methods in Chemistry, vol. 2017, Article ID 7829438, Sep. 28, 2017, pp. 1-7.

Tang et al., "A detachable coating of cholesterol-anchored PEG improves tumor targeting of cell-penetrating peptide-modified liposomes", Acta Pharmaceutica Sinica B 4.1 (2014): 67-73.

Terada et al., "Novel PEG-matrix metalloproteinase-2 cleavable peptide-lipid containing galactosylated liposomes for hepatocellular carcinoma-selective targeting", Journal of controlled release 111.3 (2006): 333-342.

Wilson et al., "Orally delivered thioketal-nanoparticles loaded with TNF$\alpha$-siRNA target inflammation and inhibit gene expression in the intestines", Nature materials 9.11 (2010): 923.

Zhang et al., "Biocompatible Reactive Oxygen Species (ROS)-Responsive Nanoparticles as Superior Drug Delivery Vehicles", Advanced healthcare materials, vol. 4, Issue 1, 2015, pp. 69-76.

Zhao et al., "Boronic Acid Shell-Crosslinked Dextran-b-PLA Micelles for Acid-Responsive Drug Delivery", Macromolecular Bioscience, vol. 14, No. 11, Nov. 2014, pp. 1609-1618.

U.S. Appl. No. 16/690,599, Non-Final Office Action, dated Mar. 12, 2021, 17 pages.

Matsumoto et al., "Safe Control of Construction-Deconstruction of High-Density Peg Brushes on the Surface of Peptide Nanospheres by Thermally Induced Shrinkage of PEG-SS-PEG", Chemistry Letters, vol. 42, 2013, pp. 344-346.

Matsumoto et al., "Safe Control of Construction-Deconstruction of High-density PEG Brushes on the Surface of Peptide Nanospheres by Thermally Induced Shrinkage of PEG-SS-PEG", Supporting Information, Chemistry Letters, vol. 42, 2013, pp. 1-10.

* cited by examiner

ROS-RESPONSIVE MULTILAMELLAR LIPOSOMAL VESICLES FOR TARGETING INFLAMMATORY MACROPHAGES

CROSS-REFERENCE TO RELATED APPLICATIONS

This application is a divisional of U.S. application Ser. No. 15/672,589, filed Aug. 9, 2017, entitled "ROS-Responsive Multilamellar Liposomal Vesicles For Targeting Inflammatory Macrophages", which claims priority to U.S. Provisional Application No. 62/372,986, filed Aug. 10, 2016, which is incorporated by reference herein in its entirety.

BACKGROUND

Inflammatory macrophages are implicated in a variety of disease states such as cardiovascular disease, diabetes, and autoimmune disease. Macrophages involved in chronic inflammation are known to release a variety of molecules and enzymes such as reactive oxygen species (ROS), chemokines, cytokines, and proteases. While nanoparticles may be used for selective delivery of agents to macrophages, it is difficult to specifically deliver particles to inflammatory macrophages. Further, nonspecific delivery of nanoparticles or systemic delivery of small molecules directly can significantly increase the toxicity burden on the body.

SUMMARY

Provided herein are liposomal vesicles comprising at least a first lipid bilayer and a second lipid bilayer and a plurality of crosslinkages between the first lipid bilayer and the second lipid bilayer, wherein the plurality of crosslinkages comprise boronic ester or thioketal bonds. Also provided are pharmaceutical compositions comprising the liposomal vesicles described herein and a pharmaceutically acceptable excipient. Also provided are methods of treating a subject with a disease comprising administering to the subject a pharmaceutical composition comprising the liposomal vesicles described herein. Methods of making multilamellar liposomal vesicles that are responsive to reactive oxygen species are also disclosed herein.

BRIEF DESCRIPTION OF THE DRAWINGS

FIG. 1A is a schematic showing an exemplary liposomal vesicle having a first lipid bilayer and a second lipid bilayer. FIG. 1B is a schematic showing the use of boronic acid to crosslink the polar head groups of the lipids between the lipid bilayers. FIG. 1C is a schematic showing the hydrolysis of the boronic ester crosslinkage in the presence of ROS (e.g. hydrogen peroxide).

DETAILED DESCRIPTION

Figure 1A:
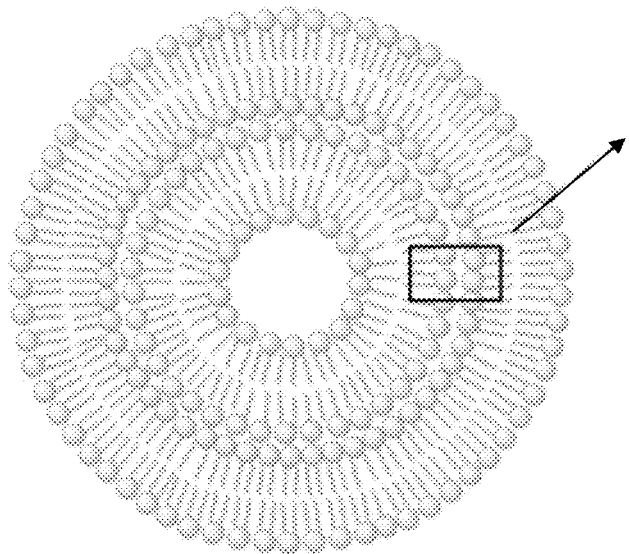
FIGS. 1A, 1B, and 1C are schematics showing an exemplary liposomal vesicle and the chemistry of ROS-responsive crosslinkages.

Liposomes are vesicles consisting of amphipathic lipids arranged in one or more bilayers. When lipids are placed in aqueous medium, the hydrophilic interaction of the lipid head groups with water results in the formation of multilamellar or unilamellar systems or vesicles which resemble biological membranes in the form of a spherical shell. Liposomes may be small (0.025-0.05 µm) to large (0.05-10 µm). Optionally, the liposomes have diameters of 50-5,000 nm or less. Thus, liposomes can be unilamellar (having one lipid bilayer) or multilamellar (having two or more lipid bilayers) and a population of liposomes can contain both unilamellar and multilamellar liposomes. See, e.g., Akbarzadeh et al., *Nanoscale Res. Letters,* 8:102-110 (2013), which is incorporated by reference herein in its entirety. Liposomal vesicles containing more than one lipid bilayer are referred to as multilamellar liposomal vesicles (MLVs). Typically multilamellar liposomal vesicles have an outer lipid bilayer encapsulating one or more inner lipid bilayers. Lipids used to prepare liposomal lipid bilayers can include, but are not limited to, phospholipids, sphingolipids, glycosphingolipids, saturated glycerides, steroids such as cholesterol, synthetic phospholipids, and combinations thereof. Optionally, one or more lipids in the lipid bilayer contains a hydroxyl group. Optionally, the lipids comprise hydrogenated soy phosphatidylcholine (HSPC), distearoyl glycerol phosphoethanolamine (DSPE), or combinations thereof. The lipids of the lipid bilayer can include one or more different types of lipids. Thus, for example, the lipid bilayer can include both HSPC and DSPE. Optionally, the lipid bilayer comprises two or more types of lipids, for example, located in proximity to each other. The composition of each bilayer in an MLV can also contain different lipids. The lipids can be packed together to form a bilayer or can be integrated into the hydrophobic portion of the bilayer. It should be noted that any lipid bilayer can be continuous or can be composed of islands of lipid bilayer. It should also be understood that the hydrocarbon chains of any of the lipids can be of the same or differing lengths.

Described herein are multilamellar liposomal vesicles, formulations comprising the multilamellar liposomal vesicles, and methods of making and using the multilamellar liposomal vesicles. Specifically, provided herein are liposomal vesicles with two or more lipid bilayers with boronic ester crosslinkages between at least two of the lipid bilayers. Optionally, the liposomal vesicles with two or more lipid bilayers have thioketal crosslinkages between at least two of the lipid bilayers. The boronic ester or thioketal crosslinkages holds the MLV together, thus, reducing the rate of release of encapsulated agents within the vesicle and increase the stability of the circulating liposomal vesicles. In the presence of reactive oxygen species (ROS), the boronic ester crosslinkages oxidize and hydrolyze, resulting in reversal of the crosslinkages and release of encapsulated agents from the liposomal vesicles. Similarly, in the presence of ROS, thioketal crosslinkages are reversed releasing encapsulated agents from the liposomal vesicles. Thus, the liposomal vesicles selectively target inflammatory macrophages and, in ROS-containing microenvironments, provide controlled, sustained delivery of agents while reducing delivery of agents to other locations. The liposomal vesicles are particularly useful for targeting and delivering agents to inflammatory macrophages, tumors and other ROS-containing microenvironments found in cancer, inflammatory diseases, and neurodegenerative diseases such as Alzheimer's disease.

As described herein, the liposomal vesicles include at least two lipid bilayers having boronic ester or thioketal crosslinkages between at least two of the lipid bilayers and, optionally, between all adjacent lipid bilayers in the vesicles. Specifically, the liposomal vesicles comprise at least a first lipid bilayer and a second lipid bilayer with a plurality of crosslinkages between the first lipid bilayer and the second lipid bilayer, wherein the plurality of crosslinkages comprise boronic ester or thioketal bonds. FIG. 1 shows the boronic ester crosslinking chemistry in multilamellar liposomal vesicles. In particular, FIG. 1A shows an example of a multilamellar liposomal vesicle having two lipid bilayers in which an inner (or first) lipid bilayer is encapsulated by an outer (or second) lipid bilayer. The hydrophilic head groups of the lipids in the adjacent outer and inner lipid bilayers can be crosslinked to form crosslinkages between the lipid bilayers. As shown in the rectangular box, the hydrophilic head groups of lipids in the lipid bilayers are separated by an interbilayer space spanned by crosslinkages. As used herein, interbilayer space, sometimes referred to as interlamellar space, refers to an aqueous space between lipid bilayers in a multilamellar liposomal vesicle, for instance between a first lipid bilayer and a second lipid bilayer. The number of interbilayer spaces increases proportionately with the number of lipid bilayers in the multilamellar liposomal vesicle. An aqueous space encapsulated by the inner-most lipid bilayer defines the inner cavity. By way of example, a multilamellar liposomal vesicle having three lipid bilayers would have an inner cavity defined by the first (inner-most) lipid bilayer, an interbilayer space between the first and second (middle) lipid bilayers, and another interbilayer space between the second and third (outer-most) lipid bilayers. The lipid bilayers are permeability barriers, which can limit the diffusion of one or more agents between the interbilayer spaces, the inner cavity, and the external environment. Thus, one or more agents can be located in the inner cavity, in one or more interbilayer spaces, or any combination thereof. The same or different agents can be located in the various locations within the liposomal vesicle, depending, for example, upon the intended order of the release of the agents or the desire to provide longer sustained release of a single agent. Optionally, one or more agents can be embedded within one or more of the lipid bilayers themselves, such that, as the lipid bilayer breaks down, the agents within the bilayer are released.

As used herein, the term crosslinkage refers to a covalent attachment bridging at least two complex molecules in the lipid bilayers. The crosslinkages described herein contain boronic ester bonds optionally formed at reactive groups, for instance hydroxyl groups, in the complex molecules. Optionally, the crosslinkages contain thioketal bonds. Optionally, the complex molecules are biological lipids, artificial lipids, steroids such as cholesterol, PEG, PEGylated molecules, glycolipids, or other complex molecules embedded in the lipid bilayers and combinations thereof. Optionally, the crosslinkages form boronic ester or thioketal bonds with the lipid head groups of lipids in the lipid bilayers. Optionally, the crosslinkages span the interbilayer space between lipid bilayers. Optionally, a crosslinkage includes a first boronic ester or thioketal bond formed at a lipid head group of a lipid in a first lipid bilayer, the crosslinkage spanning the interbilayer space, and a second boronic ester or thioketal bond formed at a lipid head group of a lipid in a second lipid bilayer. Optionally, a crosslinkage comprises two boronic ester bonds or two thioketal bonds. Optionally, the liposomal vesicle can include a plurality of crosslinkages. Optionally, the crosslinkages are between multiple adjacent lipid bilayers. By way of example, the crosslinkages in a multilamellar liposomal vesicle containing three lipid bilayers are between the first and second lipid bilayers and between the second and third lipid bilayers. Optionally, the crosslinkages are between head groups of lipids in the same lipid bilayer. By way of example, the crosslinkages are between the head group of a first lipid and the head group of a second, adjacent lipids in the same layer of a lipid bilayer, such that the crosslinkages are in the circumferential direction of the lipid bilayer. Optionally, the crosslinkages are between an adjacent pair of lipid bilayers, between multiple adjacent pairs of lipid bilayers, between lipids of the outer bilayer in the circumferential direction, between lipids of one or more bilayers in the circumferential direction, or any combination thereof. Optionally, the crosslinkages reduce the release of encapsulated agents within the multilamellar liposomal vesicle and increase the stability of the multilamellar liposomal vesicle.

Figure 1B:
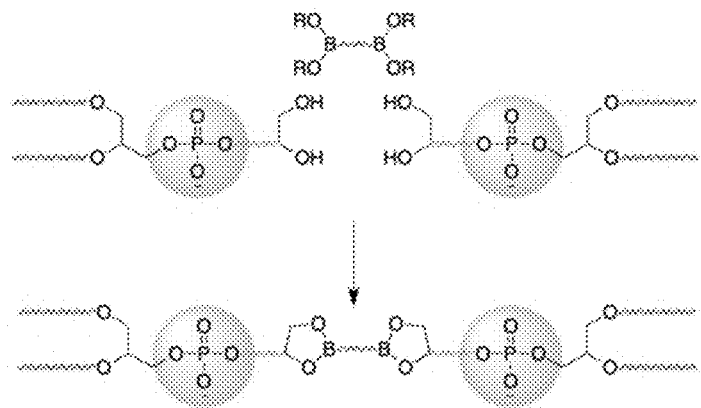

The boronic ester or thioketal crosslinkages can be formed from addition of a crosslinker to a nascent liposomal vesicle or during fusion of two or more liposomal vesicles. Optionally, the crosslinker contains at least two terminal ends having boronate centers. Boronic esters are ideal for crosslinking applications because each boronate center can form up to three ester bonds with hydroxyl groups. FIG. 1B shows an example of the boronic ester crosslinking chemistry. Addition of a crosslinker having two terminal ends with boronate centers form boronic ester bonds at each boronate center with, for instance, lipid head groups of phospholipids in adjacent lipid bilayers. The crosslinker thus bridges the interbilayer space by forming covalent ester bonds between adjacent lipid bilayers. Optionally, the crosslinker may have two or more terminal ends having boronate centers and may form boronic ester bonds. Optionally, a plurality of crosslinkages are formed from a plurality of crosslinkers. The length of the crosslinker between the terminal ends having boronate centers may be adjusted to span the interbilayer space. Optionally, the length of the crosslinker is substantially the same as the shortest distance across the interbilayer space. Non-limiting, exemplary crosslinkers that can be used to form boronic ester bonds include aryl boronic acids, phenylboronates, pyridylboronates, and cyclohexylboronates. More specifically, non-limiting, exemplary crosslinkers may include 4-bromomethylphenyl boronic acid pinacol ester, 3-(N,N-dimethylamino) phenyl boronic acid; 2,4-dichlorophenylboronic acid; 4-aminocarbonylphenylboronic acid; 3-chlorophenylboronic acid; 4-hydroxyphenylboronic acid; 4-propylphenylboronic acid; 3-[(E)-2-nitrovinyl)phenylboronic acid; 4-chlorocarbonylphenylboronic anhydride; cyclopenten-1-ylboronic acid; 2-bromopyridine-3-boronic acid; 2,4-ditert-butoxypyrimidin-5-ylboronic acid; 2,4-bis(benzyloxy)pyrimidine-5-boronic acid; 5-phenyl-2-thienylboronic acid; 5-formylthiophene-3-boronic acid; or any combination thereof. Non-limiting, exemplary crosslinkers that can be used to form thioketal bonds include $CH_2CHCONHCH_2CH_2SC(CH_3)_2SCH_2CH_2NHCOCHCH_2$; $CH_2CHCONHCH_2CH_2SC(CH_3)_2SCH_2CH_2NHCOCHCH_2$; $CH_2CHCONHCH_2CH_2SC(CH_3)_2SCH_2CH_2NHCOCHCH_2$; $CH'H''CHCONHCH_2CH_2SC(CH_3)_2SCH_2CH_2NHCOCHCH''H'$; $CH_2CHCONHCH_2CH_2SC(CH_3)_2SCH_2CH_2NHCOCHCH_2$; $CH'H''CHCONHCH_2CH_2SC(CH_3)_2SCH_2CH_2NHCOCHCH''H'$; $CH_2CHCONHCH_2CH_2SC(CH_3)_2SCH_2CH_2NHCOCHCH_2$; 3,3'-(propane-2,2-diylbis(sulfanediyl))dipropionic acid; or any combination thereof.

The liposomal vesicles described herein include reversible boronic ester or thioketal crosslinkages. As used herein, a reversible crosslinkage refers to a covalent attachment bridging at least two complex molecules in the lipid bilayers to form a covalent bond that can be chemically broken, resulting in loss of the covalent attachment between the complex molecules. Optionally, reversal of the crosslinkages releases encapsulated agents and/or decreases the stability of the lipid bilayers in the liposomal vesicle to allow leakage of agents encapsulated in the interbilayer spaces or agents embedded within the lipid bilayers (e.g., intrabilayer agents). Optionally, reversal of the crosslinkages occurs in vivo, for example, in the presence of ROS. Optionally, reversal of the crosslinkages occurs in specific organs, tissues, or cell types. Optionally, reversal of the crosslinkages occurs at or near the site of inflammatory macrophages. Optionally, reversal of the crosslinkages occurs at a faster rate at or near inflammatory macrophages than at or near the site of macrophages that are not inflammatory macrophages. Optionally, the reversal of the crosslinkages occurs or occurs at a faster rate at or near a tumor microenvironment wherein the MLVs accumulate due to the enhanced permeability and retention (EPR) effect.

Figure 1C:
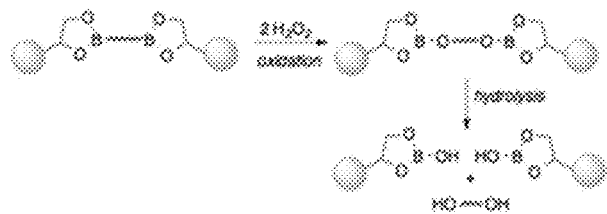

As noted above, the boronic ester or thioketal crosslinkages described herein are reversed in the presence of reactive oxygen species (ROS). As such, the boronic ester or thioketal crosslinkages may be referred to as ROS-responsive crosslinkages and the liposomal vesicles containing them as ROS-responsive liposomal vesicles. More specifically, reversal of the boronic ester crosslinkages occurs by oxidation and hydrolysis of the boronic ester bond in the presence of ROS. FIG. 1(c) shows an example of the chemistry of reversal of the boronic ester crosslinkages. In FIG. 1(c), ROS, such as hydrogen peroxide, oxidizes the boronic ester bond, which is followed by hydrolysis with water and formation of a hydroxyl group on the boron atom. The portion of the crosslinker between the hydrolyzed boronic esters forms a leaving group. Upon encountering ROS, the crosslinkages are reversed, resulting in release of encapsulated agents within the liposomal vesicles and reduced liposomal vesicle stability.

The liposomal vesicle described herein can be a multilamellar liposomal vesicle having at least a first lipid bilayer and a second lipid bilayer. A lipid bilayer is composed of two layers of amphiphilic molecules, predominantly lipids. The hydrophobic portions of the amphiphilic molecules of the bilayer project towards each other, minimizing contact with aqueous environments. The hydrophilic portions of the amphiphilic molecules form an interface with the surrounding aqueous environment. Thus, the hydrophilic surfaces of a liposomal lipid bilayer define an exterior environment and an interior, encapsulated environment. A multilamellar liposomal vesicle contains at least two lipid bilayers in which an inner lipid bilayer is encapsulated within an outer lipid bilayer. Optionally, the multilamellar liposomal vesicle may have more than two lipid bilayers. See, e.g., Akbarzadeh et al., *Nanoscale Res. Letters,* 8:102-110 (2013), which discloses the general structure of multilamellar liposomal vesicles and which is incorporated herein by reference in its entirety.

Liposomal lipid bilayers typically contain lipids as the predominant structural molecule. Lipids used to prepare liposomal lipid bilayers in a multilamellar liposomal vesicle can include, but are not limited to, phospholipids, sphingolipids, glycosphingolipids, saturated glycerides, steroids such as cholesterol, synthetic phospholipids, and combinations thereof. Optionally, the lipid contains a diol head group. Optionally, the lipids comprise palmitoyloleoyl phosphatidylglycerol (POPG). Optionally, the hydrocarbon chains of the lipids are the same length to promote symmetry in the lipid bilayers. Optionally, the lipids are modified by PEGylation.

The liposomal vesicles described herein optionally have diameters of 5,000 nm or less. The liposomal vesicles may optionally have diameters of 300 nm or more. The liposomal vesicles may optionally have diameters from 300 to 3,000 nm.

Liposomal lipid bilayers may contain one or more components in addition to the lipids. Optionally, the additional components include, but are not limited to, detergents, PEGylated molecules, protein-conjugated molecules, and molecules with aliphatic anchors. The additional components optionally are added during formation of liposomal vesicles. Optionally, the additional components are added to lipid bilayers after liposomal vesicle formation. Optionally, the additional components are inserted into lipid bilayers by, for instance, hydrophobic interaction, non-covalent attachment to lipid bilayers, or covalent attachment to lipid bilayers by, for instance, bond formation with lipid head groups. The additional components in the liposomal lipid bilayers may alter the properties of lipid bilayers, including but not limited to, membrane fluidity, permeability, flexibility, fusogenicity, stability, charge/electrostatics, and asymmetry. The additional components may also introduce or alter functional properties of the liposomal vesicles, including but not limited to, duration of circulation, targeting capabilities, degradation triggers, cellular uptake, and the like. By way of example, addition of PEG to the surface of liposomal vesicles increases the duration of circulation, whereas addition of cholesterol to fluid lipid bilayers decreases permeability and fluidity. See e.g., Bozzuto et al., *Intl J. of Nanomedicine,* 10: 975-999 (2015), which is incorporated herein by reference in its entirety.

Methods for making liposomes are known. For example, liposomes may be prepared by dissolving lipids in a solvent, which may optionally contain an emulsifier, followed by drying to form a thin lipid film. The lipid film is then hydrated to form sheets of lipid bilayers. Using hydration and agitation or sonication, for example, the lipid bilayers form spherical lipid bilayers. Fusion, extrusion, solvent addition, freeze-thaw, detergent removal, or further agitation may be used, as desired, to control liposome homogeneity in size and lamellarity. Liposomes can be made by any method known. See, e.g., Bozzuto et al., *Intl J. of Nanomedicine,* 10: 975-999 (2015); Akbarzadeh et al., *Nanoscale Res. Letters,* 8:102-110 (2013), which are incorporated herein in their entireties. The crosslinking of MLV's can be performed after MLV formation by the additional of crosslinkers or can be performed during MLV formation.

The liposomal vesicles described herein can include one or more agents. Optionally, the agent is an agent active in vivo. Suitable agents include, but are not limited to, nucleic acids, polypeptides, antibodies, small molecules, lipids, carbohydrates, and any combination thereof. The agent can be a therapeutic, chemotherapeutic, phototherapeutic, and/or diagnostic agent. Non-limiting examples of agents include a therapeutic drug or prodrug, a phototherapeutic agent (such as indocyanine green), and a diagnostic agent used, for example, for imaging. Optionally, the agent is active in a particular organ, tissue, or cell type. Optionally, the agent is active in ROS-containing microenvironments. Optionally, the agent is active on or in macrophages. Optionally, the agent is toxic to inflammatory macrophages. Optionally, the active agent is used to image areas of active inflammation, as shown by a population of inflammatory macrophages.

The agent or combination of agents may be associated with the liposomal vesicle in one or more ways. The agent or combination of agents may be directly attached to the surface of the liposomal vesicle, for instance by attachment to a lipid head in the outer lipid bilayer. Optionally, the agent or combination of agents is indirectly attached to the surface of the liposomal vesicle, for instance by non-covalent bonding or by attachment to a linker. The agent or combination of agents may be entrapped in a liposomal vesicle in one or more ways. Optionally, the agent or combination of agents is encapsulated within the liposomal vesicle. An encapsulated agent is located anywhere inside the liposomal vesicle outer-most lipid bilayer of the liposomal vesicle. The agent or combination of agents can optionally be located between lipid bilayers of the multilamellar liposomal vesicle in interbilayer spaces. For instance, the agent or combination of agents can be located between a first lipid bilayer and a second lipid bilayer. The agent or combination of agents can be embedded within the first lipid bilayer, the second lipid bilayer, both the first lipid bilayer and the second lipid bilayer, or within all of the lipid bilayers. As used herein, embedded refers to the insertion of a hydrophobic portion of a molecule into the hydrophobic region of a lipid bilayer such that the inserted molecule is stabilized in the membrane at least partially by hydrophobic interactions. One or more agents is optionally fully or partially embedded within one or more lipid bilayers. A fully embedded agent refers to an agent in which the entire structure of the agent is embedded within the hydrophobic region of a lipid bilayer. A partially embedded agent refers to an agent in which a portion of the agent is embedded within the hydrophobic region of a lipid bilayer and a portion of the agent is either embedded in the hydrophilic region of a lipid bilayer (for instance, in the lipid head groups) or protrudes from the lipid bilayer. Partially embedded agents optionally have a hydrophilic portion that interfaces with an aqueous environment from either the inner side, outer side, or both sides of a lipid bilayer. The agent or combination of agents is optionally located in an inner cavity of the liposomal vesicle. For instance, the agent may be located within the aqueous environment encapsulated by the inner-most lipid bilayer. Optionally, the agent or combination of agents is located in any one or more liposomal locations described herein, or any combination thereof. When more than one agent is used, the different agents optionally are located in the same or different locations of the liposomal vesicle. It is also appreciated that multilamellar liposomal vesicles may have heterogeneity in the amount of an agent entrapped in the multilamellar liposomal vesicles. By way of example, a multilamellar liposomal vesicle having five lipid bilayers may contain a greater amount of an agent than a multilamellar liposomal vesicle having two lipid bilayers. As another example, a multilamellar liposomal vesicle having lipid bilayers of greater diameter may contain a greater amount of an agent than a multilamellar liposomal vesicle having lipid bilayers of smaller diameter. Further, a multilamellar liposomal vesicle may contain a combination of agents located, embedded, or encapsulated in different bilayers or between different bilayers.

A multilamellar liposomal vesicle that includes ROS-responsive boronic ester or thioketal crosslinkages between lipid bilayers may carry and deliver one or more agents to one or more microenvironments containing ROS. Optionally, the one or more active agents are released in the presence of ROS. Collectively, a multilamellar liposomal vesicle containing ROS-responsive boronic ester or thioketal crosslinkages between lipid bilayers permits targeted delivery of liposomal vesicles and entrapped agents to inflammatory macrophages and ROS-containing microenvironments.

Optionally, the liposomal vesicles described herein include a targeting molecule. A targeting molecule may target a liposomal vesicle to specific sites for delivery, uptake, adhesion, degradation, and/or other functions. A targeting molecule can be a nucleic acid, polypeptide, lipid, carbohydrate, small molecule, or any combination thereof. For instance, a polypeptide targeting molecule can be an antibody or a Fab fragment of an antibody. Often, a targeting molecule is attached to the surface of a liposomal vesicle, making the targeting molecule accessible to the intended target. By way of example, an antibody may be conjugated to the surface of a liposomal vesicle such that the antibody binds a specific epitope (e.g., an epitope on an inflammatory macrophage). Optionally, a targeting molecule can be directly attached to the surface of a liposomal vesicle, for instance, by covalent attachment to a lipid head in the outer lipid bilayer. Optionally, a targeting molecule is attached by a linker to the lipid bilayer, for instance by a PEG conjugated to a lipid head group in the lipid bilayer. A targeting molecule may also be embedded within the outer lipid bilayer of a liposomal vesicle. By way of example, a targeting molecule comprising a lipid may be embedded within the lipid bilayer such that the exposed lipid head group is accessible for binding to a target. The term target refers to a molecule or molecular moiety that the targeting molecule preferentially binds. An array of antibody-epitope, ligand-receptor, enzyme-substrate, and other targeting mechanisms are known. Targeting molecules are particularly useful for enhancing the specific delivery of liposomal vesicles carrying toxic agents to a particular tissue while decreasing delivery to other tissues. Thus, targeting molecules may increase the local concentration of a drug at a desired organ, tissue, or cell type to increase the drug's effectiveness. Use of targeting molecules may also decrease the local concentration of the drug at other tissues to avoid non-specific toxicity. Suitable targeting molecules include, but are not limited to, EGFR antibodies, HER2 antibodies, EpCAM antibodies, FolR antibodies, folate, trastuzumab, and PSMA antibodies. Suitable targets include cell surface markers located on macrophages, e.g., CD11b, F4/90, CD68; CSF1R, MAC2, CD11c, LY6G, LY6C, IL-4Ra, and CD163. See, e.g., Murray and Wynn, Nature Reviews Immunology 11:723-737 (2011), which is incorporated by reference herein in its entirety.

Also described herein are pharmaceutical compositions comprising liposomal vesicles and a pharmaceutically acceptable excipient. Pharmaceutically acceptable compositions can include a variety of carriers and excipients. A variety of aqueous carriers can be used, e.g., buffered saline and the like. Liposomal vesicles may be formulated with one or more particular excipients depending on the desired route of administration. These solutions are sterile and generally free of undesirable matter. Suitable carriers and excipients and their formulations are described in Remington: The Science and Practice of Pharmacy, 22nd Edition, Lloyd V. Allen, Jr., ed., Pharmaceutical Press (2012). By pharmaceutically acceptable, used synonymously herein with physiologically acceptable and pharmacologically acceptable, is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. A pharmaceutical composition will generally comprise agents for buffering and preservation in storage and can include buffers and carriers for appropriate delivery, depending on the route of administration. Further, antimicrobial preservatives may be included in the formulation.

The compositions for administration will commonly include the liposomes and a pharmaceutically acceptable carrier, optionally an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. Oral pharmaceutical compositions optionally comprise an inert diluent or assimilable edible carrier, or they may be enclosed in hard or soft shell gelatin capsule, or they may be compressed into tablets, or they may be incorporated directly with the food of the diet. For oral therapeutic administration, the liposomal vesicles may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the liposomal vesicles of the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more concentrated or highly concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in Remington: The Science and Practice of Pharmacy, 22nd Edition, Lloyd V. Allen, Jr., ed., Pharmaceutical Press (2012).

Also provided are methods of treating a subject with a disease by administering the herein disclosed liposomal vesicles. Optionally, compositions comprising the liposomal vesicles may be administered to the subject. Methods of treating a subject can optionally include administering to the subject an effective amount of the liposomal vesicles. Optionally, the method of treating a subject includes administering to the subject a pharmaceutical composition comprising any one or more of the liposomal vesicles described herein. The subject can optionally be a mammal, for instance, a human.

The disease to be treated is optionally a disease characterized by production of reactive oxygen species (ROS). As used herein, a disease characterized by production of ROS means a disease in which more ROS is produced in the subject having the disease than in the absence of the disease. Production of ROS can be systemic or localized to a particular regions, organs, tissues, or cells (e.g., cancer cells or inflammatory macrophages). More specifically, the disease can be cancer, an inflammatory disease, or a neurodegenerative disease. The disease can be acute, chronic, recurrent, or relapsing. The ROS-responsive liposomal vesicles can specifically target a microenvironment (e.g., a tumor microenvironment) comprising ROS in a subject having the disease characterized by production of ROS. Inflammatory macrophages are known to produce ROS. Optionally, the disease is characterized by a systemic or regional increase in inflammatory macrophages. Optionally, the disease is characterized by localization of inflammatory macrophages in a microenvironment containing ROS. Optionally, the ROS-responsive liposomal vesicles specifically target inflammatory macrophages in a subject having the disease characterized by production of ROS.

As used herein, the term cancer refers to all types of cancer, neoplasm, or malignant tumors found in mammals, including leukemia, carcinomas and sarcomas. Non-limiting, exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

As used herein, the term inflammatory disease refers to all types of diseases in which one skilled in the art would recognize inflammation as a disease symptom. Non-limiting examples of inflammatory diseases include asthma, rheumatoid arthritis, osteoarthritis, gout, Alzheimer's disease, Parkinson's disease, cardiovascular disease, diabetes, lupus erythematosus, scleroderma, Sjorgen's syndrome, vasculitis, tendonitis, synovitis, sinusitis, endocarditis, osteomyelitis, hepatitis, colitis, psoriasis, chronic obstructive pulmonary disease, bronchiectasis, emphysema, silicosis, inflammatory bowel disease, ulcerative colitis, Crohn's disease, multiple sclerosis, Guillain-Barre Syndrome, myasthenia gravis, mastitis, laminitis, laryngitis, chronic cholecystitis, Hashimoto's thyroiditis, inflammatory breast disease, microbial infection, autoimmune diseases, and inflammation due to presence of foreign objects, implanted devices, transfusions or transplants.

As used herein, the term neurodegenerative disease refers to all types of diseases in which one skilled in the art would recognize neurodegeneration as a disease symptom. Non-limiting examples of neurodegenerative diseases include Parkinson's disease, Alzheimer's disease, dementia, Huntington's disease, multiple sclerosis, amyotrophic lateral sclerosis, stroke, epilepsy, diabetes, diabetes-associated peripheral neuropathy, Charcot-Marie-Tooth disease, spinocerebellar ataxias, Guillain-Barre syndrome, infectious diseases such as prion diseases, and neurodegeneration due to foreign chemical or radiological agents.

Liposomal vesicle compositions administered to a subject optionally circulate within the subject, for instance in the blood or lymph. A liposomal vesicle having an agent can deliver the agent to organs, tissues, and/or cell types throughout the subject. Surface PEGylation is known to increase the circulation time of liposomal vesicles. Such PEGylated liposomal vesicles are referred to as long-circulating liposomal vesicles. By this method, a PEGylated liposomal vesicle may act as a stable delivery vehicle for administered agents at least by contributing to the avoidance of rapid clearance of the agent and/or the avoidance of systemic toxicity of the agent. Optionally, the liposomal vesicles having boronic ester crosslinkages circulate to organs, tissues, cell types, or microenvironments containing ROS. Optionally, the liposomal vesicles having boronic ester or thioketal crosslinkages circulate to organs, tissues, or microenvironments containing inflammatory macrophages. Optionally, the liposomal vesicles cease circulation upon encountering organs, tissues, cell types, or microenvironments containing ROS or inflammatory macrophages.

As used herein, the term treat refers to any delay in onset or one or more symptoms or clinical signs, reduction in the frequency or severity of symptoms, amelioration of symptoms, improvement in patient comfort or function, decrease in severity of the disease state, etc. The effect of treatment can be compared to an individual or pool of individuals not receiving a given treatment, or to the same patient prior to or after cessation of treatment. Treatment includes partial or complete ablation of the disease. The term "prevent" generally refers to a decrease in the occurrence of a given disease (e.g., a primary cancer or metastasis). Prevention may be complete (no detectable symptoms) or partial, such that occurrence is delayed or results in fewer symptoms than would occur absent treatment.

By effective dose or amount as used herein is meant a dose of liposomal vesicles or pharmaceutical composition containing liposomal vesicles that produces the desired effect(s) (e.g., treating or preventing a disease). The exact dose and formulation of the liposomal vesicles will depend on a number of factors including the purpose of the treatment, the species of the subject, the age and weight of the subject, the disease to be treated, the severity of the disease or inflammation, and the like. Determining the dosage and formulation is ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington (2012); and Pickar, Dosage Calculations ($9^{th}$ edition) (1999)). For example, for the given parameter, a therapeutically effective amount will show a desired increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a desired 1.2-fold, 1.5-fold, 2-fold, 5-fold increase or decrease as compared to a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

The exact dose, formulation, and dosing regimen of the liposomes will depend on a number of factors including the purpose of the treatment, the species of the subject, the age and weight of the subject, the disease to be treated, the severity of the disease, the amount and type of active agent in the liposomes, and the like. Determining the dosage, formulation and dosing regimen are ascertainable by one skilled in the art using known techniques. See, e.g., Lieberman, Pharmaceutical Dosage Forms (vols. 1-3, 1992); Lloyd, The Art, Science and Technology of Pharmaceutical Compounding (1999); Remington (2012); and Pickar, Dosage Calculations ($9^{th}$ edition) (1999)). Thus, treatment may include administering a single dose or multiple dose of the liposomes or compositions containing liposomes. The liposomal vesicles or composition containing the liposomal vesicles, as disclosed herein, can be administered to the subject on a daily, twice daily, bi-weekly, monthly or any effective regimen. The treatment can be administered alone or in combination with any other treatment modalities or agents. The additional treatment can be administered simultaneously with the first treatment, at a different time, or on an entirely different therapeutic schedule (e.g., the first treatment can be daily, while the additional treatment is weekly). The course of treatment is best determined on an individual basis depending on the particular characteristics of the subject, the type of treatment selected, the type of disease treated, the age and condition of the subject, etc. The treatment, such as those disclosed herein, can be administered to the subject on a daily, twice daily, bi-weekly, monthly or any applicable basis that is therapeutically effective. The treatment may include administering a single dose or multiple doses of an effective amount of the herein disclosed liposomal vesicles. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

In the provided methods of treatment, additional active agents can be used that are suitable to the disease being treated. Thus, the provided methods of treatment optionally further comprise administering a second agent to the subject. The second agent can be associated within the liposomal vesicles, or can be disassociated with the liposomal vesicles but administered in the same composition as the liposomal vesicles. The second agent can be a therapeutic, phototherapeutic, or diagnostic agent. Suitable additional therapeutic agents include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

Optionally, the provided liposomal vesicles or compositions comprising the liposomal vesicles contain an active agent and are used for diagnosing a disease characterized by production of ROS in a subject. Thus, provided is a method of diagnosing a disease in a subject comprising administering to the subject an effective amount of the provided liposomal vesicles comprising a diagnostic agent or composition comprising the provided liposomal vesicles comprising the diagnositc agent. Administration of the liposomal vesicles or compositions diagnoses the disease or one or more symptoms of the disease in the subject. The disclosed methods may involve comparing the levels or activity of a biomarker, e.g., intracellular target of a disease, from a test sample to a control sample. As discussed above, a control sample or value refers to a sample that serves as a reference, usually a known reference, for comparison to a test sample. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. As also discussed above, diagnosis refers to a relative probability that a disease (e.g. an autoimmune, inflammatory autoimmune, cancer, infectious, immune, or other disease) is present in the subject.

The terms comparing, correlating and associated, in reference to determination of a disease risk factor, refers to comparing the presence or amount of the risk factor (e.g., amount of intracellular target of a disease) in an individual to its presence or amount in persons known to suffer from, or known to be at risk of disease, or in persons known to be free of disease, and assigning an increased or decreased probability of having/developing the disease to an individual based on the assay result(s).

Compositions comprising the herein disclosed liposomal vesicles can be delivered to a subject in a variety of ways. Compositions can be administered intravenously, intramuscularly, subcutaneously, intraperitoneally, respiratorily, dermally, orally, or combinations thereof. If the liposomal vesicles are administered in more than one dose, the liposomal vesicles may be administered by the same or by different delivery methods. The additional or second agent, if used, may be administered by the same or by different delivery methods as compared to the delivery methods used to administer the liposomal vesicles.

Also disclosed are methods for making multilamellar liposomal vesicles and, more specifically, ROS-responsive multilamellar liposomal vesicles. By way of example, the method optionally comprises (a) providing nascent multilamellar liposomal vesicles; (b) providing a plurality of boronic ester or thioketal bond-forming crosslinkers; and (c) contacting the nascent multilamellar liposomal vesicles with the crosslinkers to form multilamellar liposomal vesicles comprising a first lipid bilayer, a second lipid bilayer, and a plurality of crosslinkages between the first bilayer and the second bilayer, wherein the plurality of crosslinkages comprise boronic ester or thioketal bonds responsive to reactive oxygen species. By nascent multilamellar liposomal vesicles is meant a lipid/aqueous mixture, lipid sheets or any step in the process of organization of the multilamellar liposomal vesicles. Thus, formation of multilamellar liposomal vesicles occurs concomitantly with contacting the multilamellar liposomal vesicles with the crosslinkers.

Liposomal vesicles are typically prepared by dissolving lipids in a solvent, which may contain an emulsifier. The lipids are dried to a thin lipid film and then hydrated, which spontaneously forms sheets of lipid bilayers. Further hydration and agitation, such as by sonication, induces the lipid bilayers to enclose, forming spherical lipid bilayers. The crosslinker(s) can be added at any of these steps. Controlled agitation is required to avoid degradation, destabilization, contamination, and other complications. This process typically results in formation of multilamellar liposomal vesicles heterogeneous in size and lamellarity. As used herein, lamellarity refers to the number of lipid bilayers in a multilamellar liposomal vesicle. An increase in lamellarity indicates an increase in the number of lipid bilayers in a multilamellar liposomal vesicle. Fusion, extrusion, solvent addition, freeze-thaw, detergent removal, or further agitation may increase homogeneity in size and lamellarity, and/or improve properties such as stability and encapsulation efficiencies. Typically, MLVs are formed following hydration of a thin lipid sheet containing lipid constituents and any other desired agents, e.g., drugs or crosslinkers of interest with low energy input. The hydrophobic components are located in the film and hydrophilic components are added with the hydration buffer. MLVs can also be formed through a fusion process. Methods to construct and characterize liposomal vesicles are described, for example, in Akbarzadeh et al., *Nanoscale Res. Letters*, 8:102-110 (2013), which is incorporated herein by reference in its entirety.

The boronic ester or thioketal bond-forming crosslinkers optionally are provided as a single type of crosslinker or as two or more different types of crosslinkers. Optionally, additional components are provided to facilitate the formation of crosslinkages. Optionally, the crosslinkers are provided in a thin lipid film to be hydrated.

The contacting step occurs under conditions for forming crosslinkages between the first and second bilayer. Crosslinkages optionally form between any adjacent bilayers and/or between lipids within one or more of the bilayers. Crosslinkages may also form between head groups of lipids in the same lipid bilayer, resulting in crosslinkages in the circumferential direction of the same lipid bilayer. Crosslinkages in the circumferential direction may occur within each of the lipid bilayers of a multilamellar liposomal vesicle. Optionally, crosslinkages are between each adjacent lipid bilayer and also within the circumferential direction of each lipid bilayer of the multilamellar liposomal vesicle.

The method of making multilamellar liposomal vesicles optionally further comprises adding one or more active agents to the nascent multilamellar liposomal vesicles prior to, with, or after contacting the nascent multilamellar liposomal vesicles with the crosslinker so as to encapsulate or embed the one or more agents in the multilamellar liposomal vesicles as described herein.

The method of making multilamellar liposomal vesicles optionally further comprises fusing multilamellar liposomal vesicles containing a first agent or combination of agents with a liposomal vesicle containing an second agent or combination of agents. Optionally, the fusion is performed under conditions that result in different agents in the outer interbilayer space as compared to the inner interbilayer space or spaces.

Additional components of the lipid bilayer or agents to be added to the inner cavity or interlamellar space(s) may be added during formation of liposomes or added after formation of the liposomes. Thus, if the agent or other components are added during formation of the liposome, they are added to the nascent liposomes (e.g., to the lipid solution, to the thin lipid film, to the sheet of lipid bilayer, or during hydration or sonication).

Also described herein are kits comprising the disclosed liposomal vesicles. A typical kit comprises one or more dosage units of a composition comprising liposomal vesicles comprising reversible boronic ester or thioketal crosslinkages, or a pharmaceutically acceptable salt, prodrug, solvate, hydrate, or stereoisomer thereof. Optionally, the kit comprises instructions for use. Optionally, a single dosage unit containing one or more additional agents, may be used in combination with the disclosed compounds. Kits of the current disclosure can further comprise devices that are used to administer the active ingredients. Examples of such devices include, but are not limited to, syringes, drip bags, patches, and inhalers. The disclosed kits can further comprise pharmaceutically acceptable vehicles that can be used to administer one or more disclosed compositions. For example, if a disclosed composition is provided in a solid form that is to be reconstituted for parenteral administration, the kit can comprise a sealed container of a suitable vehicle in which the disclosed composition can be dissolved to form a particulate-free sterile solution that is suitable for parenteral administration. Examples of pharmaceutically acceptable vehicles include, but are not limited to, Water for Injection; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Formation of Liposomal Vesicles.

For the organic dissolution and film preparation of lipids, heat-treated scintillation vials were prepared. 20 ml scintillation vials are stored in an oven at 230° C. for at least 2 hours prior to film preparation. 12 (+/−0.3) mg DPPE is added to a 20 mL scintillation vial. 4 mg (400 uL) cholesterol is added from a stock solution of 10 mg/mL in 2:1 (v/v) mixture of chloroform:methanol to the 20 mL scintillation vial. 8 mg DSPE-PEG5k is added from a stock solution of 10 mg/mL in 2:1 (v/v) mixture of chloroform:methanol to the 20 mL scintillation vial. 0.4 mg DPPE-Cy5.5 is added from a stock solution of 1 mg/mL in 2:1 (v/v) mixture of chloroform:methanol to the 20 mL scintillation vial. 5 ml of 2:1 (v/v) mixture of chloroform:methanol is added to the 20 mL scintillation vial. Lipid components are dissolved, e.g., by heat application while rotating on the rotary evaporator without vacuum. The organic solvents are rotary evaporated to form a uniform lipid film around the bottom of the 20 ml scintillation vial. A vacuum is used to form a thin, uniform film. The vial is sealed with perforated parafilm and placed in desiccator for at least 2 hours to remove all volatile organics.

For lipid film hydration, 5 ml of hydration buffer (freshly prepared 10 mM pH7.4 HEPES buffer) is added to the 20 ml scintillation vial while sonicating under high heat. The samples are sonicated, vortexed, or shaken to obtain the desired size of liposome. Vortexing and gentle sonication produces larger MLVs. The particles are concentrated to approximately 3-4 mL total volume via spin filtration in 30 kDa MWCO filters. To the solution of MLVs, boronate crosslinkers or thioketal crosslinkers are added and allowed to react with the MLVs with gentle stirring for 8 hours or more. The crosslinked MLVs are purified by dialysis or spin concentration to remove any unreacted crosslinkers.

What is claimed is:

1. A method of administering a pharmaceutical composition to a subject, the pharmaceutical composition comprising:
   a liposomal vesicle comprising:
      a first lipid bilayer and a second lipid bilayer,
      a plurality of reversible crosslinkages between the first lipid bilayer and the second lipid bilayer, wherein:
         each crosslinkage of the plurality of reversible crosslinkages comprises boronic ester bonds,
         each crosslinkage is formed using a crosslinker,
         the crosslinker comprises two terminal ends, and
         each terminal end of the two terminal ends comprises a boronate center, and
      one or more active agents; and
   a pharmaceutically acceptable excipient.

2. The method of claim 1, wherein the one or more active agents are encapsulated within the liposomal vesicle.

3. The method of claim 2, further comprising releasing the one or more active agents in the presence of reactive oxygen species.

4. The method of claim 1, wherein the pharmaceutical composition comprises a plurality of liposomal vesicles.

5. The method of claim 1, wherein the subject has a disease characterized by production of reactive oxygen species.

6. The method of claim 5, wherein the disease characterized by production of reactive oxygen species is cancer, an inflammatory disease, or a neurodegenerative disease.

7. The method of claim 6, wherein the liposomal vesicle targets inflammatory macrophages.

8. The method of claim 1, wherein each crosslinkage of the plurality of reversible crosslinkages is reversed in the presence of reactive oxygen species.

9. The method of claim 1, wherein the crosslinker comprises an aryl boronic acid.

10. The method of claim 1, wherein each crosslinkage comprises two boronic ester bonds.

11. The method of claim 1, wherein administering to the subject the pharmaceutical composition comprises delivering the pharmaceutical composition intranasally.

12. The method of claim 1, wherein administering to the subject the pharmaceutical composition comprises delivering the pharmaceutical composition orally.

13. The method of claim 1, wherein administering to the subject the pharmaceutical composition comprises delivering the pharmaceutical composition parenterally.

14. The method of claim 6, wherein the disease is cancer.

15. The method of claim 6, wherein the disease is the inflammatory disease.

16. The method of claim 15, wherein the one or more active agents comprise an anti-inflammatory agent.

17. The method of claim 6, wherein the disease is the neurodegenerative disease.

18. The method of claim 1, wherein the crosslinker comprises a phenylboronate.

19. The method of claim 1, wherein the crosslinker comprises a pyridylboronate.

20. The method of claim 1, wherein the crosslinker comprises a cyclohexylboronate.

* * * * *